US012690958B2

(12) United States Patent　　　　(10) Patent No.:　US 12,690,958 B2
Camkiran et al.　　　　　　　　　　(45) Date of Patent:　　　Jul. 28, 2026

(54) EMBOLISM PROTECTION DEVICE FOR INTRODUCING INTO AN AORTIC ARCH

(71) Applicant: Protembis GmbH, Aachen (DE)

(72) Inventors: Murat Camkiran, Alsdorf (DE); Karl Von Mangoldt, Aachen (DE); Michael Pfennig, Aachen (DE); Conrad Rasmus, Berlin (DE); Oliver Schumacher, Aachen (DE)

(73) Assignee: Protembis GmbH, Aachen (DE)

( * ) Notice: Subject to any disclaimer, the term of this patent is extended or adjusted under 35 U.S.C. 154(b) by 399 days.

(21) Appl. No.: 17/621,822

(22) PCT Filed: Jun. 29, 2020

(86) PCT No.: PCT/EP2020/068252
　　§ 371 (c)(1),
　　(2) Date: Dec. 22, 2021

(87) PCT Pub. No.: WO2020/260695
　　PCT Pub. Date: Dec. 30, 2020

(65) Prior Publication Data
　　US 2022/0370186 A1　　Nov. 24, 2022

(30) Foreign Application Priority Data

Jun. 28, 2019　　(DE) ..................... 10 2019 117 603.4
Apr. 20, 2020　　(DE) ..................... 10 2020 110 712.9

(51) Int. Cl.
　　*A61F 2/01*　　　　(2006.01)
　　*A61F 2/95*　　　　(2013.01)
　　　　　　(Continued)
(52) U.S. Cl.
　　CPC .............. *A61F 2/013* (2013.01); *A61F 2/011* (2020.05); *A61F 2/9517* (2020.05); *A61F 2/966* (2013.01);
　　　　　　(Continued)

(58) Field of Classification Search
　　CPC ........ A61F 2/013; A61F 2/011; A61F 2/9517; A61F 2/966; A61F 2250/0096; A61B 2017/00243
　　See application file for complete search history.

(56) References Cited

U.S. PATENT DOCUMENTS 5,624,396 A　*　4/1997　McNamara ............ A61B 17/22
　　　　　　　　　　　　　　604/93.01
5,997,557 A　　12/1999　Barbut et al.
　　　　　　(Continued)

FOREIGN PATENT DOCUMENTS

CN　　　102256566 A　　11/2011
CN　　　105392432 A　　3/2016
　　　　　　(Continued)

OTHER PUBLICATIONS

Shimon, D. V., et al., "Aortic embolic protection device filter-transcatheter treatment for prevention of cardioembolic stroke", Abstracts / Cardiovascular Revascularization Medicine, vol. 9, 2008, 1 page.
　　　　　　(Continued)

*Primary Examiner* — Richard G Louis
(74) *Attorney, Agent, or Firm* — Knobbe, Martens, Olson & Bear, LLP

(57) ABSTRACT

The invention concerns an embolic protection device for inserting into an aortic arch to prevent embolisms. The invention moreover concerns a handle for such an embolic protection device, as well as a system consisting of a handle and/or embolic protection device and/or a catheter. Through the invention, an embolic protection device for inserting into an aortic arch, comprising a filtering unit and a feeding unit, is provided, wherein the filtering unit comprises a frame and a filter mesh, and the filter mesh is placed on the frame, the filtering unit has a proximal area and a distal area, wherein the filtering unit is designed in such a way that it can, at least (Continued)

Figure 1:
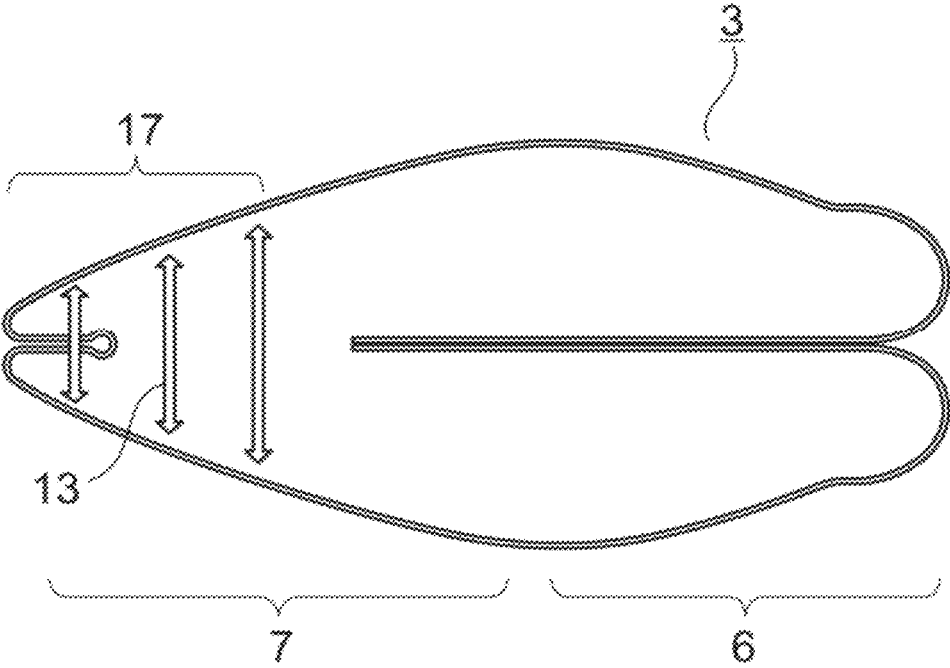

partially, be positioned in the aortic arch, and wherein, once the filtering unit is appropriately positioned, haptic and/or visual feedback is generated, which signals to the user the final position.

22 Claims, 22 Drawing Sheets

(51) Int. Cl.
  *A61F 2/966* (2013.01)
  *A61B 17/00* (2006.01)
(52) U.S. Cl.
  CPC .............. *A61B 2017/00243* (2013.01); *A61F 2250/0096* (2013.01)

(56) References Cited

U.S. PATENT DOCUMENTS

| | | | |
|---|---|---|---|
| 6,258,120 | B1 | 7/2001 | Mckenzie et al. |
| 6,361,545 | B1 | 3/2002 | Macoviak et al. |
| 6,682,543 | B2 | 1/2004 | Barbut et al. |
| 7,232,453 | B2 | 6/2007 | Shimon |
| 8,062,324 | B2 | 11/2011 | Shimon et al. |
| 8,114,114 | B2 | 2/2012 | Belson |
| 8,460,335 | B2 | 6/2013 | Carpenter |
| 9,968,359 | B2 | 5/2018 | Jösson |
| 10,485,647 | B2 | 11/2019 | Gera et al. |
| 10,500,033 | B2 | 12/2019 | Naor et al. |
| 10,512,468 | B2 | 12/2019 | Jösson |
| 10,575,852 | B2 | 3/2020 | Jösson |
| 10,610,229 | B2 | 4/2020 | Jösson |
| 10,856,961 | B2 | 12/2020 | Shemesh et al. |
| 11,000,357 | B2 | 5/2021 | Ashkenazi et al. |
| 11,534,284 | B2 | 12/2022 | Schumacher et al. |
| 11,850,137 | B2 | 12/2023 | Ashkenazi |
| 2002/0111666 | A1* | 8/2002 | Hart .......................... A61F 2/95 623/1.11 |
| 2002/0169437 | A1 | 11/2002 | Macoviak et al. |
| 2003/0171803 | A1 | 9/2003 | Shimon |
| 2004/0049207 | A1 | 3/2004 | Goldfarb et al. |
| 2004/0215167 | A1 | 10/2004 | Belson |
| 2005/0137696 | A1 | 6/2005 | Salahieh et al. |
| 2005/0209634 | A1 | 9/2005 | Brady et al. |
| 2006/0015138 | A1 | 1/2006 | Gertner |
| 2006/0161241 | A1 | 7/2006 | Barbut et al. |
| 2006/0253148 | A1 | 11/2006 | Leone et al. |
| 2007/0270901 | A1* | 11/2007 | Shimon ..................... A61F 2/01 606/200 |
| 2008/0065145 | A1 | 3/2008 | Carpenter |
| 2008/0147111 | A1 | 6/2008 | Johnson et al. |
| 2010/0010535 | A1 | 1/2010 | Mujkanovic |
| 2010/0076482 | A1 | 3/2010 | Shu et al. |
| 2010/0114017 | A1* | 5/2010 | Lenker ................. A61B 17/221 606/200 |
| 2010/0179583 | A1 | 7/2010 | Carpenter et al. |
| 2010/0185231 | A1 | 7/2010 | Lashinski |
| 2010/0324589 | A1 | 12/2010 | Carpenter |
| 2011/0022076 | A1 | 1/2011 | Lashinski |
| 2011/0213459 | A1 | 9/2011 | Garrison et al. |
| 2012/0041471 | A1 | 2/2012 | Kassab et al. |
| 2012/0172919 | A1 | 7/2012 | Fifer et al. |
| 2012/0179033 | A1 | 7/2012 | Merhi |
| 2013/0103075 | A1 | 4/2013 | Wang et al. |
| 2013/0123835 | A1 | 5/2013 | Anderson et al. |
| 2014/0031857 | A1 | 1/2014 | Richardson |
| 2014/0074148 | A1 | 3/2014 | Glenn et al. |
| 2014/0074152 | A1 | 3/2014 | Shezifi et al. |
| 2014/0100597 | A1 | 4/2014 | Wang et al. |
| 2014/0163603 | A1 | 6/2014 | Zajarias |
| 2014/0243879 | A1 | 8/2014 | Rothstein et al. |
| 2015/0039016 | A1 | 2/2015 | Naor et al. |
| 2015/0066075 | A1 | 3/2015 | Russell et al. |
| 2015/0209131 | A1 | 7/2015 | Fifer et al. |
| 2015/0230910 | A1 | 8/2015 | Lashinski |
| 2015/0313701 | A1* | 11/2015 | Krahbichler .............. A61F 2/01 606/300 |
| 2016/0106531 | A1 | 4/2016 | Shezifi |
| 2016/0175084 | A1 | 6/2016 | Johnson et al. |
| 2016/0235515 | A1 | 8/2016 | Merhi |
| 2016/0262864 | A1 | 9/2016 | Von Mangoldt et al. |
| 2016/0302909 | A1 | 10/2016 | Kelly |
| 2016/0310255 | A1 | 10/2016 | Purcell et al. |
| 2016/0317277 | A1 | 11/2016 | Carpenter et al. |
| 2016/0324621 | A1 | 11/2016 | Shezifi et al. |
| 2017/0143356 | A1 | 5/2017 | Zandi et al. |
| 2017/0165046 | A1 | 6/2017 | Johnson et al. |
| 2017/0189160 | A1 | 7/2017 | Krahbichler |
| 2018/0168538 | A1 | 6/2018 | Stigall et al. |
| 2018/0168793 | A1 | 6/2018 | Lees et al. |
| 2019/0000605 | A1 | 1/2019 | Krahbichler |
| 2019/0307545 | A1* | 10/2019 | Schumacher ........... A61F 2/011 |
| 2020/0054434 | A1 | 2/2020 | Gera et al. |
| 2021/0085445 | A1 | 3/2021 | Ashkenazi et al. |
| 2022/0370187 | A1 | 11/2022 | Camkiran et al. |
| 2023/0121543 | A1 | 4/2023 | Schumacher et al. |
| 2023/0414336 | A1 | 12/2023 | Shezifi et al. |

FOREIGN PATENT DOCUMENTS

| | | | |
|---|---|---|---|
| EP | 1014888 | A1 | 7/2000 |
| EP | 2059292 | A2 | 5/2009 |
| EP | 2337521 | A1 | 6/2011 |
| EP | 2391303 | A2 | 12/2011 |
| EP | 2661305 | A1 | 11/2013 |
| EP | 2387427 | B1 | 8/2014 |
| EP | 2777653 | A1 | 9/2014 |
| EP | 2800602 | A1 | 11/2014 |
| EP | 2822503 | A2 | 1/2015 |
| EP | 2693984 | B1 | 4/2015 |
| EP | 2859864 | A1 | 4/2015 |
| EP | 2919706 | A1 | 9/2015 |
| EP | 2996630 | A2 | 3/2016 |
| EP | 2999428 | A2 | 3/2016 |
| EP | 2537488 | B1 | 4/2016 |
| EP | 3060164 | A1 | 8/2016 |
| EP | 3476365 | B1 | 12/2024 |
| JP | 2010-526583 | A | 8/2010 |
| JP | 2012-501704 | A | 1/2012 |
| JP | 2016-533228 | A | 10/2016 |
| JP | 2017-516609 | | 6/2017 |
| JP | 2022-538308 | A | 9/2022 |
| JP | 2022-538309 | | 9/2022 |
| RU | 2518457 | C2 | 6/2014 |
| RU | 2599592 | C2 | 10/2016 |
| WO | 02/47539 | A2 | 6/2002 |
| WO | 2007/129323 | A2 | 11/2007 |
| WO | 2008/033845 | A2 | 3/2008 |
| WO | WO 2008/137177 | A2 | 11/2008 |
| WO | 2010/009042 | A1 | 1/2010 |
| WO | WO 2010/026240 | A1 | 3/2010 |
| WO | 2010/081025 | A1 | 7/2010 |
| WO | 2010/088520 | A2 | 8/2010 |
| WO | 2011/034718 | A2 | 3/2011 |
| WO | 2012/085916 | A2 | 6/2012 |
| WO | 2012078794 | A1 | 6/2012 |
| WO | 2012/152761 | A2 | 11/2012 |
| WO | 2013/126618 | A1 | 8/2013 |
| WO | WO 2015/055605 | A1 | 4/2015 |
| WO | 2015177322 | A1 | 11/2015 |
| WO | 2018077458 | A1 | 5/2018 |
| WO | 2020-260696 | A1 | 12/2020 |
| WO | WO 2020/260695 | A1 | 12/2020 |

OTHER PUBLICATIONS

Shimon, D. V., et al., "Aortic Embolic Protection Device", Sagax Medical Technologies, Subsidiary of MIV Therapeutics Inc., TCT 2006, 2006, 64 pages.
Shimon, D. V., et al., "Cardioembolic protection by AEPD", Presentation EuroPCR 2008, 2008, 2008, 21 pages.
WO 2018077458 A1 Espacenet translation (Year: 2018).

(56)         References Cited

OTHER PUBLICATIONS

Notice of Reasons for Refusal, re JP Application No. 2024-101002, dated Oct. 21, 2025.
Office Action, re CN Application No. 202211602859.0, dated Dec. 25, 2025.

* cited by examiner a)        b)        c)

28          31          31          27

43

39

EMBOLISM PROTECTION DEVICE FOR INTRODUCING INTO AN AORTIC ARCH

The invention concerns an embolic protection device for inserting into an aortic arch to prevent infiltration of particles or other debris into the cerebral vascular system. The invention moreover concerns a handle for such an embolic protection device, as well as a system consisting of said handle and a catheter, a system consisting of said handle and the embolic protection device, a system consisting of the embolic protection device and a catheter, and a system consisting of a handle, an embolic protection device and a catheter, as well as a method of using an embolic protection device, a method of using a handle and a method of using a system consisting of an embolic protection device and/or a handle and/or a catheter.

The scope of application is medicine, in particular heart surgery and interventional cardiology.

The risk of ischaemic brain lesions, right up to strokes, is one of the most feared complications heart surgery, in particular in the case of minimally invasive procedures, such as transcatheter aortic valve implantation (TAVI).

During such procedures, macroscopic particles may become detached, and then reach the brain via branches of the aortic arch, where they trigger embolisms.

Embolic protection devices which can be inserted into the aortic arch as filters when carrying out heart surgery and interventional operations, in order to prevent such particles from penetrating the branched vessels, are already known from the prior art.

What is, however, problematic, in this respect, is the correct positioning of the filters in the aortic arch. If there are small gaps, the particles can already pass by the filter, which is why high requirements need to be posed of the fit. In addition, it is not apparent to the user whether the filter is accurately placed, so that it is difficult to assess when the optimum final position has been reached. Further factors, such as the tiniest distortion of the catheter in relation to the feeding unit, can make it difficult to position the filter exactly.

The task of the invention was therefore to provide an improved embolic protection device.

The task is resolved through the features of Claim 1 and the further independent claims. The sub-claims concern advantageous enhancements of the invention.

Through the invention, an embolic protection device for inserting into an aortic arch, comprising a filtering unit and a feeding unit, is provided, wherein the filtering unit comprises a frame and a filter mesh, and the filter mesh is arranged on the frame. The filtering unit has a proximal area and a distal area, wherein the filtering unit is designed in such a way that it can, at least partially, be positioned in the aortic arch.

Advantageous is the ability to position the embolic protection device through a connection to a feeding unit to be controlled, formed via an area. By connecting the frame with the feeding unit via an area, it is made possible for adjustments to be made to the positioning of the filter in an unfolded state.

It is advantageous that, when the filtering unit is appropriately positioned, haptic or visual feedback is generated, which signals the final position to the user.

Advantageously, the user can thus feel whether the embolic protection device is positioned precisely. The embolic protection device can be designed in such a way that the haptic and/or visual feedback is generated if the filtering unit has taken up its place in the aortic arch.

The haptic feedback is in particular generated by the high anatomical adaptation of the filtering unit. The filtering unit responds once it has reached its optimum position, when it is pulled by the user, with a certain degree of resistance, and thus signals that it fits into the aortic arch precisely. Alternatively, or cumulatively, a visual check can be provided for, by attaching radio-opaque markers.

Besides the correct positioning, supported by haptic and/or visual feedback, a stable location during the placement period and minimised interaction with the respective indexing procedure are of critical significance for the functionality of the embolic protection device.

An increased stability of the embolic protection device can, inter alia, be implemented by means of an optimised fit of the filtering unit in regard to the placement environment. In addition, the radial rigidity of the embolic protection device can be implemented by reinforcement in the proximal area and residual stress in the frame (torsion).

Also advantageous for the functionality of the embolic protection device is the independence of the stable location of the embolic protection device during the placing of interventional equipment, which is needed for the indexing procedure. This is likewise implemented by means of an optimised fit. A further advantageous minimisation of the potential interaction is implemented through the placing of the proximal area of the embolic protection device in the feeder vessel. It is especially advantageous, in this respect, that the proximal end of the embolic protection device disappears into the feeder vessel, due to this configuration, and thus no edge is formed between the embolic protection device and the roof of the aortic arch, but a smooth transition is implemented.

The feeding unit within the meaning of the invention is a device for transmitting forces to the filtering unit, through which the filtering unit can, inter alia, be pulled or pushed through the catheter and moved within the aortic arch. This is preferably designed, in the embolic protection device, as a wire, preferably a coil consisting of multiple thin wires. Further embodiments are conceivable.

The embolic protection device is, advantageously, designed in such a way that the frame comprises two ends in the proximal area, which extend in parallel to one another in the interior of the frame and are connected with the feeding unit via an area. Thus, the filtering unit can be led through a catheter by means of the feeding unit, and moved in the aortic arch.

In one embodiment of the invention, the proximal area of the filtering unit contains an anchorage, by means of which the radial rigidity of the frame is increased. This contributes towards a more stable positioning and stronger feedback of the haptic signal.

In a further embodiment of the embolic protection device, the distal area is designed to be tapered towards the tip, and thus has a streamlined cross-sectional distribution. This leads to a better geometric adaptation of the distal tip to the aortic arch, and reduces the contact surface in the bloodstream when being placed. The gradual increase in the contact pressure on the aortic arch is simultaneously implemented.

A support can be placed on the filter mesh of the embolic protection device, which is connected with the feeding unit, either directly or via the ends of the frame, and through which the filter mesh in the expanded state is passively drawn to the aortic roof.

Such support is, advantageously, constructed from a force element, such as a spring or also a flexible material, such as silicone or rubber.

In an alternative embodiment, the filter mesh may also be connected with a device through which the filter mesh can be actively drawn to the aortic roof.

The device is preferably constructed in such a way that it can be routed through the catheter, independently of the feeding unit, to the handle area, and can be actively operated there by the user. Various materials come into question for this. Preferably, a wire or yarn can be used.

In an also independently inventive embodiment, the embolic protection device is designed in such a way that the proximal area can be configured separately from the distal area within the feeder vessel, and the distal area separately from the proximal area within the aortic arch. The frame is thus divided into a proximal vascular section and a distal aortic section.

This embodiment has the advantages at potential interactions with devices that are used in the aortic arch are reduced.

In the process, the geometry of the aortic section remains free from impact, which can be implemented by a powerful modification of the direction of curvature in the filter frame. The frame is thus divided into a proximal vascular section and a distal aortic section.

Due to the independent design of the vascular and aortic sections and their anatomical fit, the filtering unit may be fixed in the feeder vessel and in the aortic arch in such a way that haptic and/or visual feedback is received when it is precisely positioned.

This embodiment has the advantages that potential interactions with devices that are used in the aortic arch are reduced.

In an alternative, likewise independent, inventive embodiment, the embolic protection device is characterised by the entire filtering unit being able to be configured entirely in the aortic arch. Provided that the positioning of the filtering unit in the aortic arch is done appropriately, the proximal area is formed distally in regard to the feeder vessel. In that respect, after unfolding the filtering unit under tension after it has been inserted into the aortic arch, a filtering surface extending in the direction of flow is formed, which, by drawing the frame towards the roof of the aortic arch using the feeding unit, causes the cerebral vessels to be covered.

One variant of the embolic protection device is preferably designed in such a way that the ends of the frame are, in the unfolded state, placed at an obtuse angle W3 to the proximal filtering level, so that, by drawing the frame towards the roof of the aortic arch, a proximal filtering surface extending in the direction of flow is formed.

The contact pressure of the proximal end against the aortic arch wall is thereby improved, which leads to a reduction in the interactions with devices which are, for example, used to carry out the TAVI procedure.

Due to the position of the complete filtering unit in the aortic arch and in the proximal area beyond the feeder vessel, a haptic signal is generated by the feeding unit upon pulling the filtering unit, which haptic signal signals the correct positioning of the filtering unit.

Figures 9A, 9B, 9C:
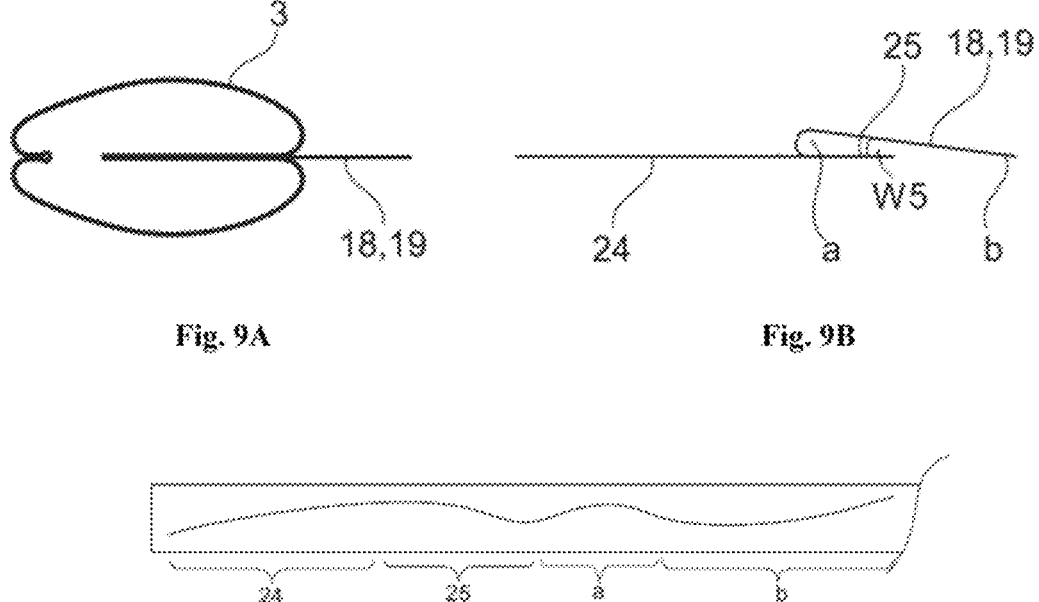

In a further variant, the proximal area is divided into two sections, in such a way that the ends of the proximal area delineate an arcuate shape in such a way that the first part of the arcuate shape is formed in the direction of the distal area, and the second part in the direction of the proximal area—see FIG. 9c).

It is advantageous, in this respect, that the second part forms an acute angle extending downwards W5, as, when the embolic protection device is placed in its final position, the former presses the end of the proximal area against the roof of the aortic arch. The haptic feedback is reinforced in the process, while the interaction with other devices is further reduced.

In a further advantageous embodiment of the invention, the ends of the frame may, when the filtering unit is in the unfolded state, be placed at an acute angle W1 to the distal filtering level (see FIG. 11a)), so that, by drawing the frame towards the roof of the aortic arch, the frame is formed in such a way that the width of the end of the proximal area is increased. In a special embodiment, this is implemented by it being possible to arrange the ends of the frame in such a way that they are submerged under the filtering level at the joint to the proximal frame (see FIG. 11b)), whereby a tension can be transferred to the frame, which results in an enlargement of the proximal area, if the latter is drawn in the direction of the feeder vessel.

In another embodiment, the filtering unit is divided into two sections in such a way that the proximal area protrudes from the filtering level, so that, through the proximal area being transformed, a torsion is transferred to the distal area when the device is positioned, which increases the contact pressure to the roof of the aortic arch.

Alternatively, the filtering unit of the embolic protection device is divided into two sections in such a way that the proximal area protrudes from the filtering level, so that the proximal area widens when the device is positioned.

A torsion may, moreover, form in the frame, in such a way that the distal end buckles against the aortic roof.

Through this arrangement, when the filtering unit is successfully positioned haptic feedback is passed on to the user.

A further effect is that the cerebral vessels are better covered.

In a further, also independently inventive, advantageous embodiment of the invention, the filtering unit of the embolic protection device may be divided into two sections in such a way that, when the embolic protection device is removed, the proximal area can be actively and/or passively collapsed, independently of the distal area.

In a further variant, the filtering unit is divided into two sections, in such a way that the ends of the proximal area delineate an arcuate shape in such a way that the first part of the arcuate shape is formed in the direction of the distal area, and the second part in the direction of the proximal area.

In a special embodiment, the proximal area can be bent in the direction of flow, independently of the distal area. In a preferred embodiment, both the distal area and the proximal area can be bent by 5° to 85°, especially preferably by 25° to 75° and quite especially preferably by 60°, in relation to the feeding unit. This particularly preferably concerns the proximal frame.

In a special embodiment, the lateral areas can be bent at an angle perpendicular to the direction of flow, independently of one another. In a preferred embodiment, the bending is at an angle of between 5° and 85°, especially preferably 25° to 75° and quite especially preferably 60° in relation to the feeding unit.

This leads to the blood vessels being better covered, a more stable position and more pronounced haptic feedback.

In a further, also independently, inventive variant of the embolic protection device, the filtering unit is divided into two sections in such a way that the proximal area and the distal area each have their own frame, over which their own respective filters are stretched.

The embolic protection device is preferably characterised in that the second part of the ends of the frame is connected, through a device, with the filter mesh and/or the proximal frame, and the proximal area can be actively collapsed, in the direction of the feeder vessel, through said device. Thus, the device can be removed again via the catheter without trouble.

The embolic protection device can, however, also be designed in such a way that the filtering unit is divided into two sections in such a way that the proximal area and the distal area each have their own frame, and that an individual filter is stretched over both frames. With this embodiment, a support is preferably placed between the filter mesh and/or the frame of the proximal area, through which the proximal frame can be passively collapsed in the direction of the feeder vessel. The removal of the device is thereby facilitated.

As an alternative, which is also independently inventive, the filtering unit of the embolic protection device may be divided into two sections in such a way that a second frame lies in the outer area of the first frame, and the second frame is only connected to the filter mesh in the distal area of the first frame, and the proximal end of the first frame can be pulled in the direction of the feeder vessel, wherein the second frame is drawn towards the roof of the aortic arch, with a wedge emerging.

The first frame is preferably constructed of a thicker wire than the second frame, as it can be actively moved and takes the second frame with it. The formation of a wedge is especially advantageous, as the branched vessels can be well covered through this flexible system.

An alternative enhancement is constituted by an embolic protection device in which the frame of the filtering unit is connected with a return device, through which the frame can be returned into the catheter, and the circumference of the filter mesh exceeds the circumference of the frame, wherein the filter mesh is connected with the feeding unit, so that, when the filter mesh is pulled in the direction of the feeder vessel, a funnel is formed.

In this variant, an independent frame, without a stabilising connection to the feeding unit, is used. Since the adaptation to the aortic arch is implemented via the filter mesh, the frame can be formed in various ways, for example it may be round or oval. The removal of the frame from the aortic arch is implemented by an independent return device, preferably a wire, which is either connected to the feeding unit or is returned to the user separately for active operation.

The filtering unit is pulled through the feeding unit to the feeder vessel. Alternatively, it can, however, also be equipped with an independent active device.

The design of the funnel leads to optimum coverage of the branched vessels. When the device is ideally positioned, also in these embodiments a haptic signal is transmitted to the user.

A further, also independently inventive, aspect concerns a handle for an embolic protection device, characterised in that the handle comprises a first connecting piece, a handle shell, a slide and/or a second connecting piece, wherein the first connecting piece is designed as a connection that is to be actively secured and/or the second connecting piece is designed as a reversible clamping connection.

In a further embodiment, the handle is characterised in that the handle comprises a first connecting piece, a handle shell, a slide and/or a second connecting piece.

In that regard, the first connecting piece may be designed as a connection that is to be secured actively or passively, and/or the second connecting piece may be designed as a permanent clamping connection.

The handle enables various functions. For instance, a fixed connection to a catheter can be produced. This is preferably implemented by the first connecting piece being designed in such a way that a connection to be actively secured to a catheter can be produced. For that purpose, a luer-lock connection can be produced between the catheter and the first connecting piece. The connecting piece preferably has notches on the inside, into which the blades of the catheter can be inserted. In that respect, the sleeve of the first connecting unit can be pushed onto the catheter. This leads to better handling of the embolic protection device, as the catheter is fixed, and thus protected against rotation.

By means of the second connecting piece, a reversible clamping connection to the feeding unit can be produced, in order to transfer tractive or compressive force and moments to the feeding unit.

The handle may, moreover, include a slide, which is designed in such a way that it can exert a tractive and/or compressive mechanism, for loading and positioning devices. The slide will preferably be equipped with a locking device, which enables the position of the slide to be adjusted in relation to the handle shell. In that respect, the slide can be fixed reversibly, for instance in the end position, to lock devices after preparing them prior to use. In one embodiment, a push button can be placed on the handle, with a detent on the slide, for this purpose.

The handle shell is preferably designed in a form-fit manner and non-rotatably in relation to the slide. In this respect, it would make sense for the slide not to have a round geometry.

These features of the handle have proven advantageous when using, for example, an embolic protection device, as the smallest movements may lead to problems in inserting, positioning and removing the filtering unit, as well as a transfer of rotational movements being essential for positioning devices.

Another preferred enhancement of the invention consists in the handle containing a haemostatic valve, which is preferably configured in the front area of the handle. This haemostatic valve may contain a rinsing option.

The handle shell may, moreover, have an interior guide tube, which can be inserted into the slide. The guide tube serves to guide the feeding unit, in order to prevent the feeding unit from buckling when pressure is transferred to it through the slide being pushed forward in the interior of the handle portion.

The invention further concerns a system consisting of the embolic protection device and a catheter. Advantageously, the embolic protection device is designed, in this system, in such a way that it can be passed through the catheter.

Another enhancement of the invention concerns a system consisting of a handle and a catheter.

This system is especially preferred as a unit with a non-reversible joint, but a reversible joint is also possible. For example, for positioning other interventional equipment.

The handle and catheter may in particular be an integral unit, or be reversibly connected with one another. Said unit may additionally be reversibly, or also non-reversibly, connected with the embolic protection device during manufacture.

In another enhancement of the invention, this concerns a system consisting of an embolic protection device and a handle.

The invention likewise concerns a system consisting of the embolic protection device, the handle and a catheter. In that respect, the catheter may be designed to be fixed in the handle, and the embolic protection device designed to be able to pass through the catheter, and be capable of being connected with the handle via the feeding unit. This system is especially preferably envisaged as a unit with non-reversible connections between the catheter and the handle, as well as between the handle and the embolic protection device, but reversible connections are also possible.

A likewise independently inventive subject of the invention is a method for positioning the embolic protection device using the device. The method is characterised in that, when the filtering unit is appropriately positioned, haptic and/or visual feedback is generated, which signals the final position to the user.

By exerting tractive and/or compressive forces on the feeding unit, and, if applicable, further active devices, it is possible to insert the filtering unit into the aortic arch, position it in the ideal way, and remove it.

Further independent inventive aspects of the invention concern a method of using an embolic protection device, a method of using a handle and a method of using a system consisting of an embolic protection device and/or a catheter and/or a handle. In particular, the method can be used for rotational adjustment of the distal area, in particular while the filter is being positioned, through the handle being rotated and moments being transferred through the reversible clamping connection, and thus the feeding unit, as well as the simultaneous transmission of moment via the catheter, and thus via the friction joint to the folded filter.

The invention in particular concerns an embolic protection device for inserting into an aortic arch, comprising a filtering unit and a feeding unit, wherein the filtering unit comprises a frame and a filter mesh, and the filter mesh is arranged on the frame. The filtering unit has a proximal area and a distal area, wherein the filtering unit is designed in such a way that it can, at least partially, be positioned in the aortic arch.

In a preferred embodiment, the embolic protection device is characterised in that, when the filtering unit is appropriately positioned, haptic and/or visual feedback is generated, which signals the final position to the user.

In a further embodiment, the embolic protection device is characterised in that the frame comprises two ends in the proximal area, which extend in parallel to one another in the interior of the frame and are connected with the feeding unit. The two ends are, for example, shown in FIGS. 1, 2 and 4, the connection with the feeding unit in FIG. 10 or in FIG. 10, by way of example, in the state positioned in the aortic arch.

The embolic protection device in accordance with the invention may, ideally, comprise a frame with two ends in the proximal area, which extend in parallel to one another in the interior of the frame and are connected with the feeding unit via an area. Shown, for example, in the expanded state in FIG. 8A and in detail in FIG. 8C.

The proximal area preferably has an anchorage, designed in such a way that the radial rigidity is increased. Such an anchorage may, in that respect, be a crimp sleeve, a wire coil, welded connection, a thread, etc. It is essential, at this point, that the ends of the wire can be fixed to one another (see FIG. 4).

In an alternative, also independently inventive, embodiment, the embolic protection device is constructed in such a way that the distal area is designed to taper towards the tip, and thus having a streamlined cross-sectional distribution. Shown in FIG. 1.

In an alternative in accordance with the invention, the embolic protection device is characterised in that the proximal area can be adjusted to the feeder vessel through a change in the direction of curvature in the frame geometry, and can be fixed therein.

In one variant, a support (21) can be configured within the embolic protection device in accordance with the invention between the filter mesh and the feeding unit, through which the filter mesh is passively drawn to the aortic roof in the expanded state.

Said support may be a spring, elastic material such as rubber or nitinol, preferably a pre-formed nitinol geometry or similar.

In a further variant, the embolic protection device is characterised in that the filter mesh is connected with a device, so that the filter mesh can be actively drawn to the aortic roof via the device.

Such a device may be a wire or a yam or other material which is suitable for use in the body and with which the filter mesh can be positioned.

The embolic protection device is preferably designed in such a way that the proximal area can be configured separately from the distal area in the feeder vessel, and the distal area separately from the proximal area in the aortic arch.

In an alternative in accordance with the invention, the embolic protection device is characterised. in that the proximal area can be adjusted to the feeder vessel through a change in the direction of curvature in the frame geometry, and can be fixed therein.

Figure 10:
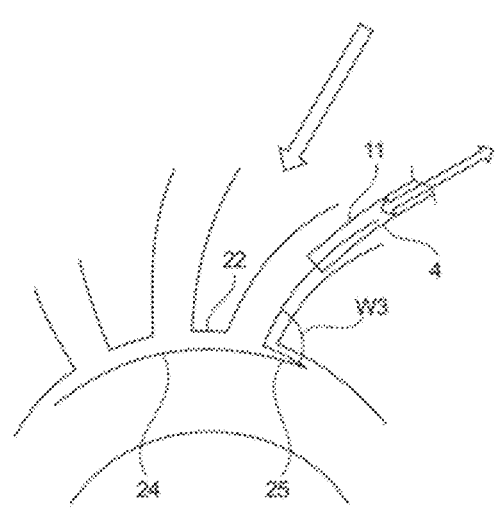

The embolic protection device is preferably designed in such a way that the complete filtering unit can be placed in the aortic arch, and wherein, when the filtering unit is appropriately positioned in the aortic arch, the proximal area is placed downstream from the feeder vessel, taking the direction of flow of the blood as a starting point (see FIG. 10).

In another variant, the ends of the proximal area may be divided into a first part and a second part.

The embolic protection device is preferably constructed in such a way that, in the unpositioned state, the ends of the proximal area define an arcuate shape, wherein the first part a, of the arcuate form is formed in the direction of the distal area, and the second part b, in the direction of the proximal area. (See FIG. 9b).

In a further special embodiment, the embolic protection device is characterised in that, in the unfolded state, the ends of the frame are placed at an acute angle W1 to the distal filtering level, so that, by drawing the frame towards the roof of the aortic arch with the proximal area that has disappeared under an angle W4, the latter is formed in such a way that the end of the proximal area widens. Said widening generates torsion in the wire, which causes the distal end to fold upwards. Shown in FIG. 11.

In this variant of the embolic protection device, the proximal area protrudes from the proximal filtering level, so that, through the proximal area being transformed (when the device is positioned), a torsion is transmitted to the distal area, which increases the contact pressure on the roof of the aortic arch.

In a preferred embodiment, the embolic protection device is designed in such a way that the ends of the frame are, in the unfolded state, placed at an obtuse angle W3 to the proximal filtering level, so that, by drawing the frame towards the roof of the aortic arch, a proximal filtering surface extending in the direction of flow is formed (see FIG. 10). Especially preferably, the distal end folds upwards, once the proximal end is drawn towards the aortic roof.

Figure 12:
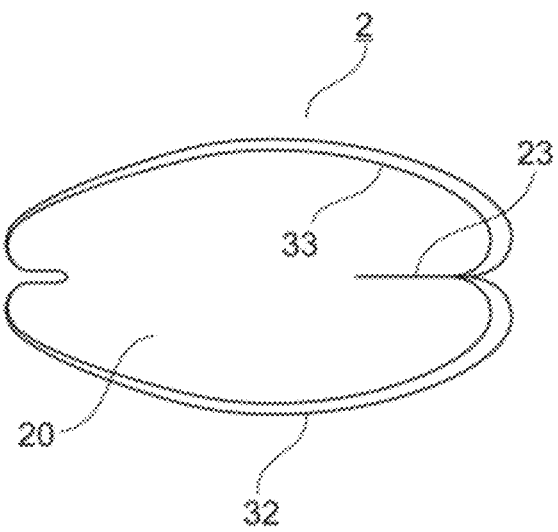

In an especially preferred embodiment, the embolic protection device is constructed in such a way that the filtering unit is divided into two sections, in such a way that a second frame lies in the outer area of the first frame (see FIG. 12).

Said embolic protection device is preferably characterised in that the first frame is only connected with the filter mesh in the distal area of the second frame.

In these embodiments, the proximal end of the first frame can be drawn in the direction of the feeder vessel, wherein in this way the second frame is drawn towards the roof of the aortic arch, and a formation of the filter mesh arises, for example in the form of a wedge.

Alternatively, the frame of the filtering unit may be connected with a return device, through which the frame can be returned into the catheter, and the surface of the filter mesh exceeds the stretched surface of the frame, wherein the filter mesh is connected with the feeding unit, so that, when the filter mesh is pulled in the direction of the feeder vessel, a funnel is formed.

A further inventive aspect concerns a handle for a medical device, characterised in that the handle comprises a first connecting piece, a handle shell, a slide and/or a second connecting piece, wherein the first connecting piece is designed as a connection that is to be actively secured and/or the second connecting piece is designed as a reversible clamping connection.

In a further embodiment, the handle is characterised in that the handle comprises a first connecting piece, a handle shell, a slide and/or a second connecting piece, wherein the first connecting piece is designed as a connection to be passively secured and/or the second connecting piece is designed as a permanent clamping connection.

The handle enables various functions. For example, a fixed connection to a catheter or another medical device can be produced. This is preferably implemented by the first connecting piece being designed in such a way that a connection to be actively secured, for example to a catheter or another device, can be produced. For that purpose, a Icier-lock connection can be produced between the catheter and the first connecting piece. In one variant, the connecting piece has notches on the inside, into which the blades of the catheter can be inserted. In that respect, the sleeve of the first connecting unit can be pushed onto the catheter. This leads to better handling of the embolic protection device, as the catheter is fixed, and thus protected against rotation.

By means of the second connecting piece, a reversible clamping connection to the feeding unit can be produced, in order to transfer tractive or compressive force and moments to the feeding unit.

The handle may, moreover, include a slide, which is designed in such a way that it can exert a pulling and/or pressure mechanism, for loading and positioning devices. Said pressure mechanism may, for example, be implemented by an interior guide, which prevents the feeding unit from being subject to compression or corrugation.

The handle shell preferably has an interior guide tube, which can be inserted into the slide. This may serve as a guide tube for connected medical devices, such as catheters, and prevents, inter alia, the buckling of such devices when pressure is transferred.

The slide will preferably be equipped with a locking device, which enables the position of the slide to be adjusted in relation to the handle shell. In that respect, the slide can be fixed reversibly, for instance in the end position, to lock devices after preparing them prior to use. In one embodiment, a push button can be placed on the handle, with a detent on the slide, for this purpose.

The handle may further contain a haemostatic valve. Rinsing operations can, inter also be carried out via this valve.

The invention moreover concerns a system consisting of the embolic protection device, the handle and a catheter.

Especially preferred is a system in which the embolic protection device is put in position in the handle/catheter combination in advance. In one variant of the invention, the system contains a fixed, non-reversible connection between the handle and the catheter, and a fixed, non-reversible connection to the feeding unit.

The subject of the invention is likewise a method of using an embolic protection device.

A further subject of the invention is a method of using a handle.

A method of using a system consisting of an embolic protection device of a handle and/or a catheter is also the subject of the invention.

In particular, the method can be used for rotational adjustment of the distal area, in particular while the filter is being positioned, through the handle being rotated and moments being transmitted through the reversible clamping connection, and thus to the feeding unit, as well as the simultaneous transmission of moment via the catheter, and thus via the friction joint to the folded filter.

Further details of the invention can be inferred from the exemplary embodiments, which are described below based on the figures. Any further details of the invention cited are not limited to the exemplary embodiments specified, but may also occur individually, selectively jointly, or overall in other exemplary embodiments.

Figure 2:
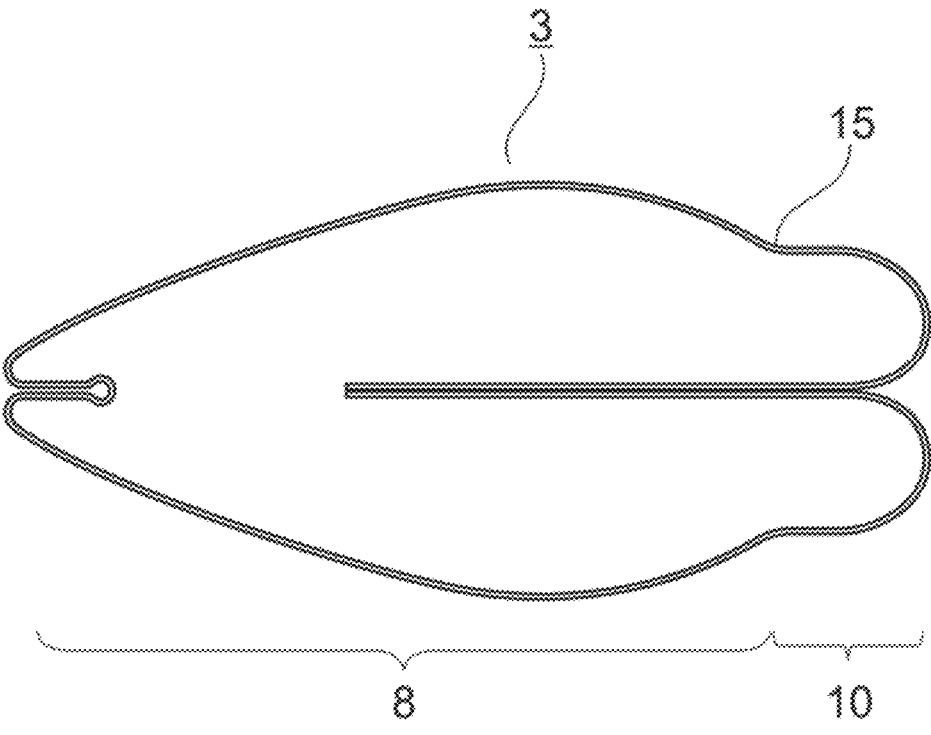
Figure 3:
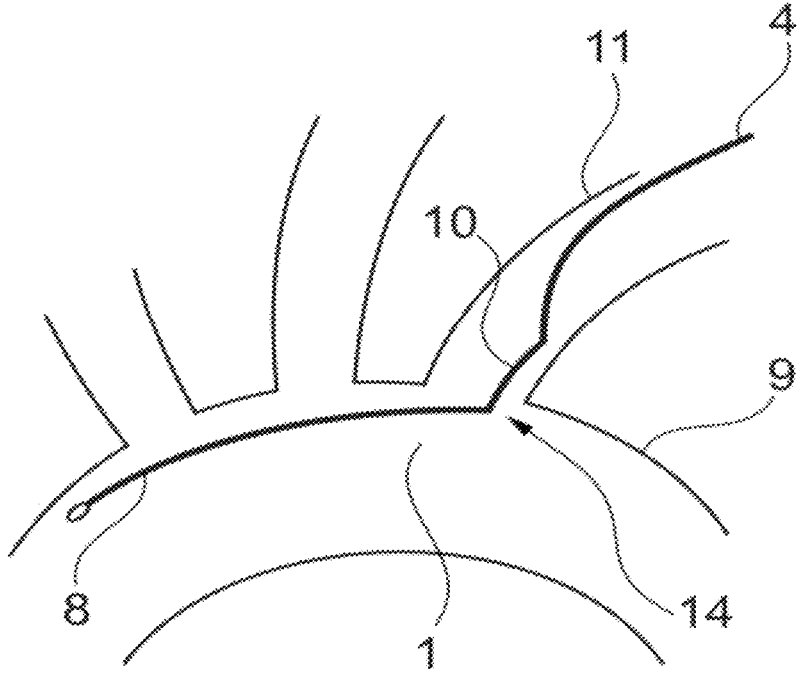
Figure 4:
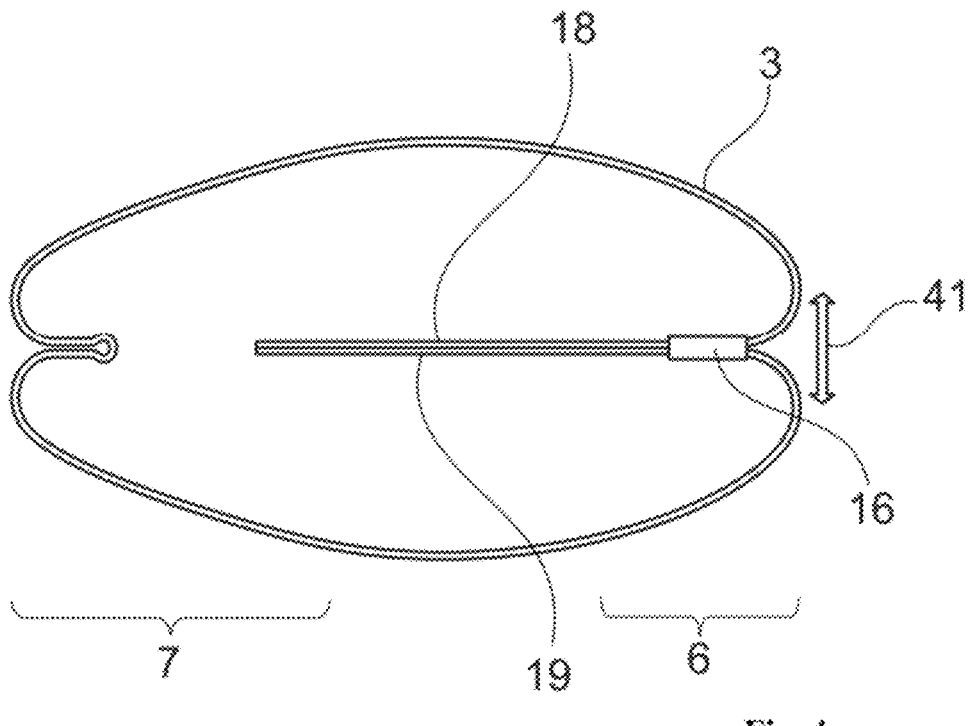
Figure 5:
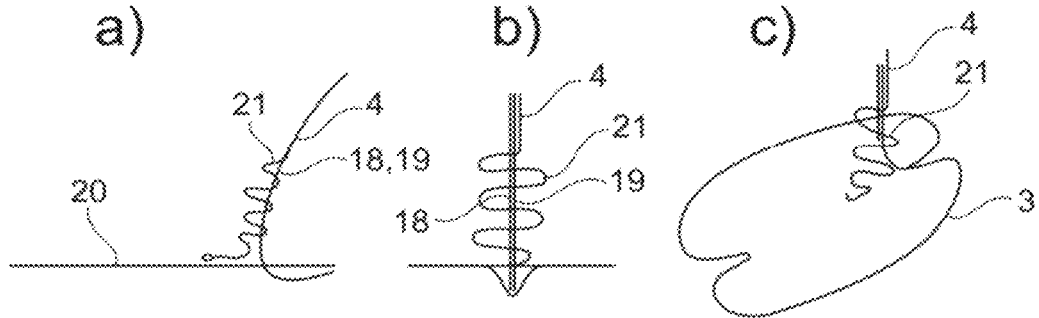
Figure 6:
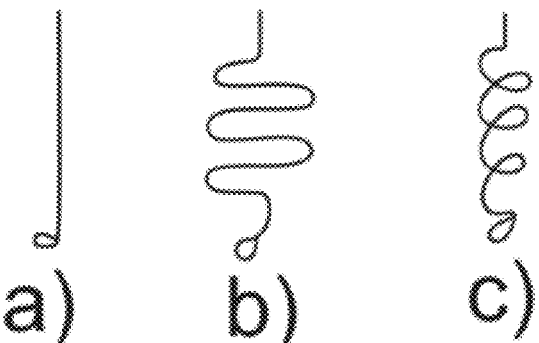
Figure 7:
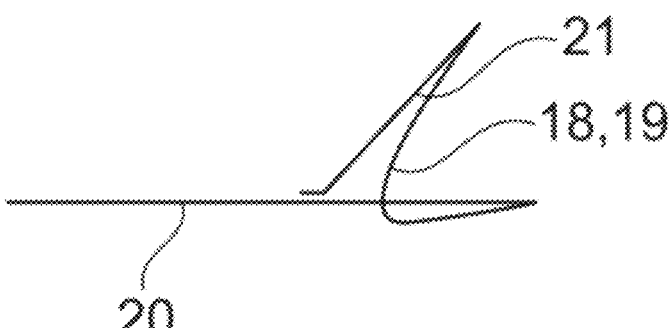
Figures 8A, 8B, 8C:
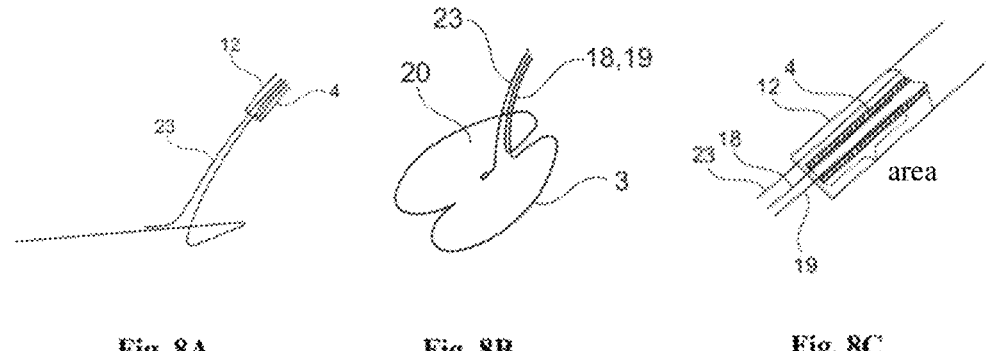
Figure 11:
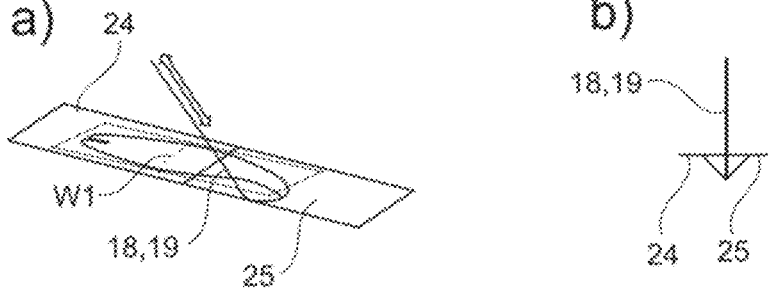
Figure 11:
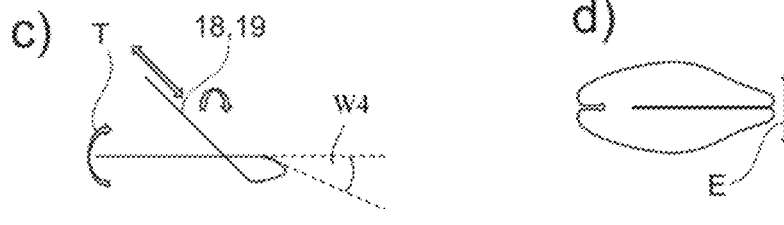

The following are shown:

FIG. 1: View from above of the frame of the embolic protection device with a tapered tip;

FIG. 2: View from above of the frame of the embolic protection device with separation into an aortic section and a vascular section;

FIG. 3: Cross-section through the aortic arch with a positioned embolic protection device with the frame from FIG. 2;

FIG. 4: View from above of the frame of the embolic protection device with a radially stabilising anchorage;

FIG. 5: Configuration of the passive filter mesh support in a) lateral view; b) frontal view; and c) perspective view, slanted from the front and the top;

FIG. 6: Examples of passive filter mesh support a) c) as a lateral view;

FIG. 7: Configuration of the passive filter mesh support as a lateral view;

FIG. 8A: Configuration of the active filter mesh support as a lateral view;

FIG. 8B: Configuration of the active filter mesh support, perspective view, slanted from the front and the top;

FIG. 8C: Detailed representation of the connection of the frame to the feeding unit FIG. 9: Frame of the embolic protection device for complete positioning in the aortic arch, with ends pointing in the direction of flow, in a) view from above, b) lateral view; and c) in the folded state in the catheter FIG. 10: Cross-section through the aortic arch with a positioned embolic protection device from FIG. 9;

FIG. 11: Frame of the embolic protection device with submerged proximal filtering level a) perspective view of the frame obliquely from the rear above, b) frontal view, c) lateral view, d) view from above FIG. 12: View from above of the filtering unit with double (first and second) frames FIG. 13: Perspective lateral view obliquely from above of the embolic protection device with expanded funnel shape.

Figure 14:
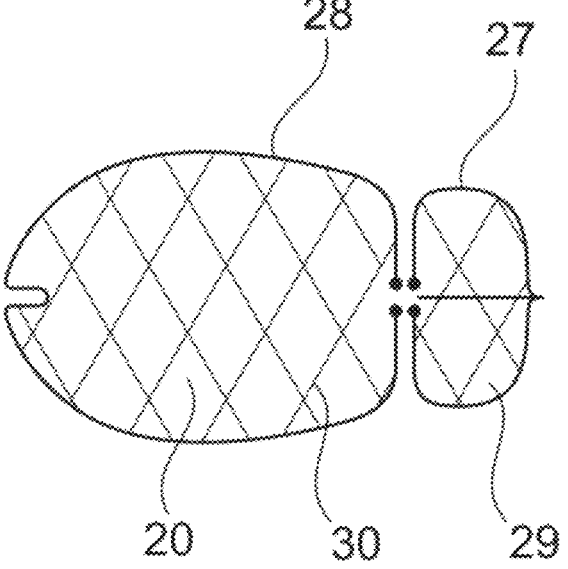
Figure 19:
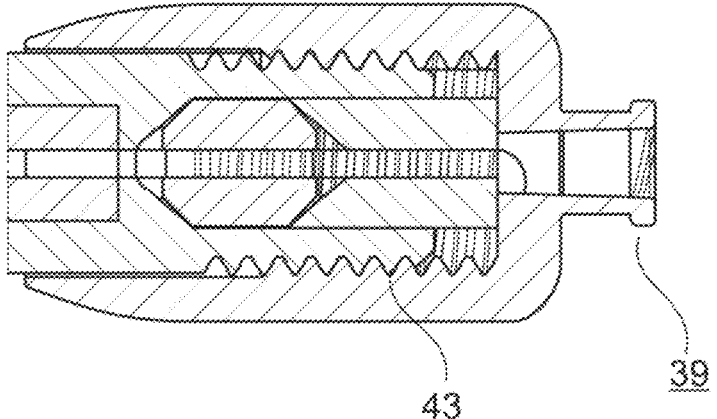
Figure 20:
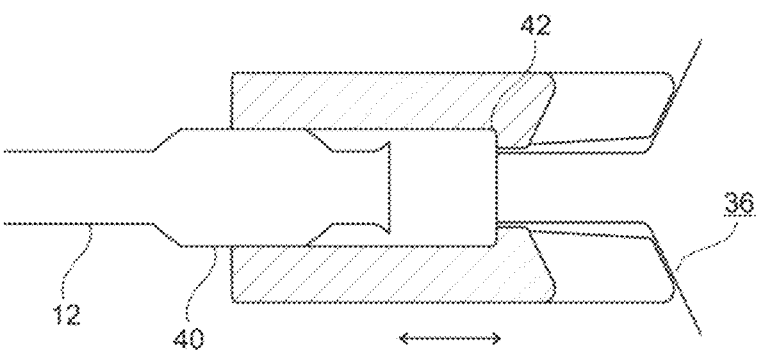
Figure 21:
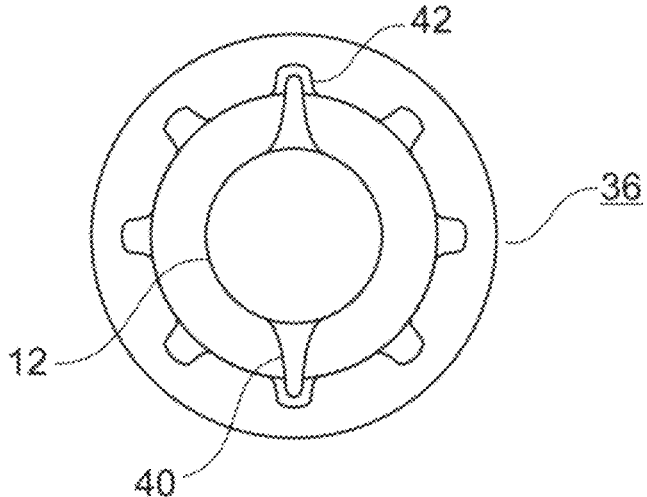

FIG. 14: View from above of the embolic protection device with frame divided into two sections and separated filters FIG. 15: View from above of the embolic protection device with frame divided into two sections and integral filter FIG. 16A: Lateral view of the embolic protection device with filter divided into two sections and active retraction of the proximal area FIG. 16B: Frontal view of the embolic protection device with filter divided into two sections and active retraction of the proximal area FIG. 16C: View of the embolic protection device in the folded stale when inserting and removing it FIG. 17A: Lateral view of the embolic protection device with filter divided into two sections in the unfolded state FIGS. 17B and 17C: Lateral view of the positioning of the embolic protection-device in the catheter upon insertion FIG. 17B and removal FIG. 17C FIG. 18A: Lateral view of the handle with extended slide FIG. 18B: Perspective representation obliquely from the front of the first connecting piece of the handle;

FIG. 19: Cross-section through the lateral view of the second connecting piece of the handle;

FIG. 20: Cross-section through the lateral view of the first connecting piece of the handle;

FIG. 21: Cross-section through the frontal view of the first connecting piece of the handle.

Figure 22:
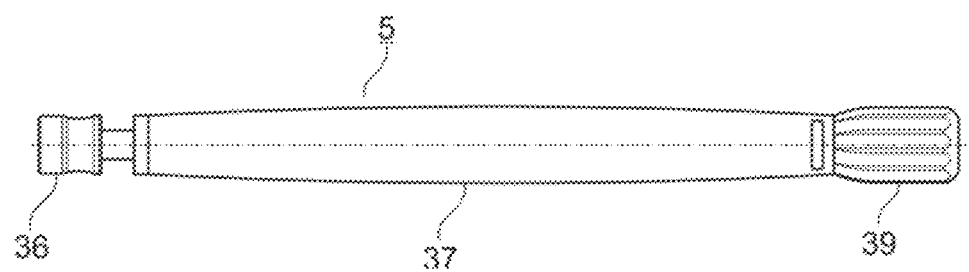

FIG. 22: Lateral view of the handle

FIG. 1 shows the view from above of the frame 3 of the embolic protection device 1, which comprises a distal area 7 and a proximal area 6. With this embodiment, the frame 3 is formed with a tapering distal tip 17. This leads to a streamlined cross-sectional distribution, designated by the arrows 13, being achieved, in order to implement the gradual rise in the contact pressure on the aortic arch 9. That leads to a reduction in the contact surface in the bloodstream when the device is positioned, it also leads to an improved adaptation of the geometry of the distal tip 17 on the aortic arch.

FIG. 2 likewise shows a view from above of the frame 3 of the embolic protection-device 1 including separation into an aortic section 8 and a vascular section 10. Said separation is implemented through a powerful modification of the direction of curvature being formed in the filter frame geometry on the frame 3 at Position 15. This results in the frame being separated into an aortic section8 in the distal area 7 and a vascular section 10 in the proximal area 6, in such a way that when the vascular section 10 is drawn into the feeder vessel 11, the geometry of the aortic section remains unaffected.

In FIG. 3, a cross-section through the aortic arch 9 with a positioned embolic protection device 1 with the frame 3 from the embodiment from FIG. 2 can be seen. The figure shows how the aortic section 8 is positioned in the distal area 7 of the frame 3 in the aortic arch, and the vascular section 10 is fixed, in the feeder vessel 11, in the proximal area 6 of the frame 3. The proximal area 6 of the frame 3 is connected with the feeding unit 4, via which the filtering unit 2 is positioned. The withdrawal of the vascular section 10 into the feeder vessel 11 serves to reduce any possible interactions with devices that are used in the aortic arch 9.

The arrow shows the position of the reduced interaction with devices in the aortic arch 9 through the vascular section 10 withdrawn into the feeder vessel H. The proximal area 6 is designed for good anatomical adaptation.

A further advantageous embodiment is shown in the example of FIG. 4, of a view from above of the frame 3 of the embolic protection device 1 with a radially stabilising anchorage. Here the two loose ends of the frame 18 and 19 are shown, which are connected at the far end of the proximal area 6 by an anchorage 16. This leads to a radially stabilising frame geometry, in order to enable haptic feedback when the filtering unit 2 is positioned correctly in the aortic arch 9, as well as a stable position during the period of application.

The area of radial stability 41 can be found at the proximal end. In this embodiment, the design of the proximal and the distal frame geometry is identical, in order to generate a synchronous distribution of force.

FIG. 5 shows the configuration of the passive filter mesh support 21 in a) lateral view; b) frontal view; and c) perspective view, obliquely from the front and the top. The passive support 21 is placed at the ends of the frame 18 and 19, which is connected to the feeding unit 4. On the other side, the support 21 is connected with the filter mesh 20 and, in the expanded state, passively draws the filter material towards the roof of the aortic arch 22 (not shown). Besides better covering of the branched vessels, in order to prevent macroscopic particles from entering these vessel brandies, a more stable position of the embolic protection device 1 is also implemented.

In FIG. 6, some examples of such a support 21 are shown, in a lateral view. In that respect, in a), the lateral view of a flat spring element is shown, as in b), and in c) a coil spring. Other materials for the support may be silicones, rubber or other elastic synthetics, as well as moulded nitinol geometries.

In FIG. 7, the configuration of the support 21 based on a flexible material, in a lateral view at the ends 18 or 19 and on the filter mesh 20 is shown. The anchorage on the filter mesh 20 leads directly to the branched vessels being better covered, as the filter mesh 20 is more elastic than the frame 3, and can develop a certain additional tension to the frame 3.

In FIG. 8A, the configuration of the active filter mesh support in the form of a device 23, from a lateral view, is shown. The device 23 is likewise connected with the filter mesh 20, is, however, actively operated by the user. It is likewise, like the feeding unit 4, arranged in the catheter 12. When it is actively pulled in the direction of the arrow, the filter mesh 20, and thus also the frame 3, is drawn towards the roof of the aortic arch 22.

In FIG. 8B, the configuration of the device 23 is shown in perspective, obliquely from the front and obliquely from above. It is apparent in both figures that the device 23 is not connected with the feeding unit 4 here, but is being conducted, independently, to the user, and, from there, can be independently operated by the feeding unit 4.

FIG. 8C shows a section of the connection of the frame ends with the feeding unit.

FIG. 9 shows the frame 3 of the embolic protection device 1 for the execution of the complete configuration of ends 18 and 19 in the aortic arch 9 pointing in the direction of flow in a) view from above, b) lateral view and c) in a withdrawn state.

The ends 18 and 19 are bent, in the relaxed state, toward the proximal filtering level 25, so that, as shown in FIG. 9b), an acute angle W5 emerges between the distal filtering level 24 and where the ends 18 and 19 meet the frame. In other words, the ends 18 and 19 of the proximal area 6 define an arcuate shape, so that the first part, a, of the arcuate shape is formed in the direction of the distal area 7 and the second part, b, in the direction of the proximal area 6.

In other words, in the relaxed state (outside the body) the ends 18 and 19 of the proximal area 6 define an arcuate shape (FIG. 9b). Said arcuate shape can be divided into a Part a and a Part b, wherein Part a of the arcuate shape is formed in the direction of the distal area 7 and the second part, Part b, in the direction of the proximal area 6, forming an acute angle W5 to one another.

The ends 18 and 19 are, when inserted into the catheter 12 (FIG. 9c) arranged in the catheter in parallel to the proximal filtering level 25 and the distal filtering level 24.

When the catheter 12 is left by thrust by means of the feeding unit 4, the frame takes on its final form, and can be positioned by being pulled by the feeding unit 4 in the aortic arch 9, so that Part a of the proximal area 6 is placed behind the feeder vessel 11, and Part b lies in the actual feeder vessel. When the feeding unit 4 is retracted, a haptic signal is generated in this way, which signals the final position to the user.

In FIG. 10, the embolic protection device from FIG. 9 is shown in the final position as a cross-section through the aortic arch 9. In the unfolded state, the ends 18 and 19 of the frame 3 are arranged in relation to the proximal filtering level 25 at an obtuse angle W3.

By drawing the frame 3 towards the roof of the aortic arch 22, a filtering surface extending in the direction of flow is formed, which causes the cerebral vessels to be covered. Thus, the interaction to the TAVI procedure is also reduced by the improved contact pressure of the proximal area 6 in relation to the roof of the aortic arch 22.

FIG. 11 shows a further embodiment of the invention and its frame geometry. Shown are the frame 3 of the embolic protection device 1 in a) a perspective view of the frame 3 obliquely from the rear above, b) frontal view, c) lateral view and d) view from above.

It is recognisable that the ends 18 and 19 of the frame 3 in the unfolded state are arranged at an acute angle W1 to the distal filtering level 24, especially preferably to the proximal filtering level 25 (shown in the figure), so that, by drawing the frame 3 towards the roof of the aortic arch 22, the latter is moulded in such a way that the width of the end of the proximal area 6 is increased.

This widening, after the positioning on the aortic arch 9 (see Arrow E in FIG. 11d), is implemented by the proximal frame from the filtering level (shown by the angle W4 in FIG. 11c) being submerged, and results in a frame torsion which, in turn, leads to the distal area being elevated (likewise shown by the rotation arrow T in Fig. c).

Due to this elevation of the distal area it can be positioned in a more stable manner. In addition, due to the increase in the width it is made possible for the cerebral vessels to be covered better, and haptic and/or visual feedback is generated which signals the final position to the user.

A view from above of a filtering unit 2 with a double frame 3 is shown in FIG. 12. A second frame 32 can be found outside a first frame 33. The distal end of both frames (32, 33) is connected with the filter mesh 20. The proximal end of the first frame 33 is not connected with the filter mesh 20, so that, through the proximal end of the first frame 33 being actively retracted, using a device 23, at the proximal end in the direction of the feeder vessel 11, a wedge created from the filter mesh 20 emerges, which minimises the interaction with devices in the aortic arch 9.

In addition, the second frame 32 is drawn towards the roof of the aortic arch 22, and thus an improved adaptation to the aortic arch 9 is achieved.

Figure 13:
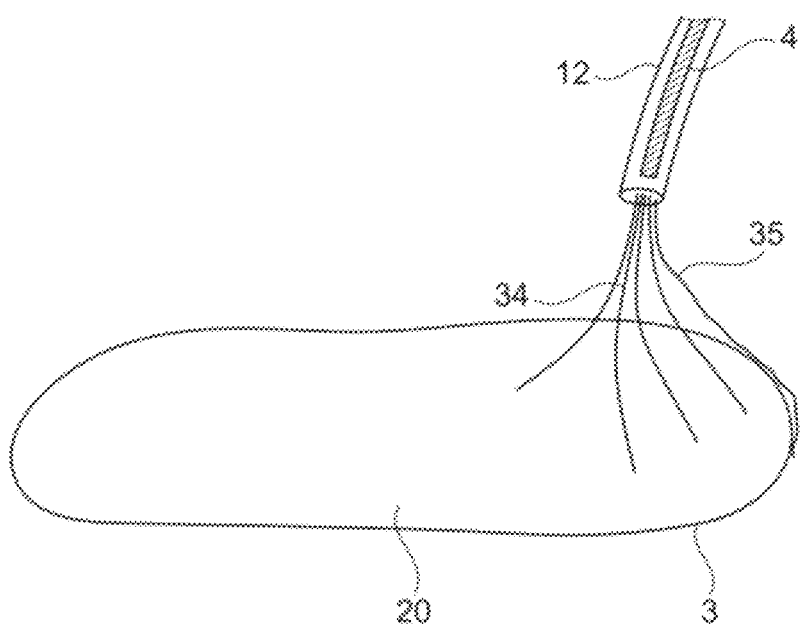

FIG. 13 shows a perspective lateral view obliquely from above of the embolic protection device 1 with a stretched funnel shape for an embodiment with a filter mesh 20, the circumference of which exceeds the circumference of the frame 3, and is thus not clamped. Said filter mesh 20 is connected with the feeding unit 4, so that, when the filter mesh 20 is pulled in the direction of the feeder vessel 11, a funnel 34 is formed. As a result, the frame 3 is likewise pulled to the aortic arch wall, which ensures that the vessel branches are very well covered.

The frame is connected with a return device 35, with which the frame can be returned into the catheter 12.

The frame 3 itself is not otherwise equipped with any further stabilising device in relation to the feeding unit 4.

FIG. 14 shows a filtering unit 2 of an embolic protection device 1 including a frame divided into two sections and a filter divided into two sections. In the view from above of the embolic protection device including a filter divided into two sections shown, it can be seen that the frame 3 is divided into a distal frame 28 and a proximal frame 27 with a distal filter 30 and a proximal filter 29.

Through the division of the frame, the existence of four ends emerges (designated with dots that run parallel to one another and/or protrude from the frame plane at a perpendicular angle (in their extension, not shown), so that four wires in total are connected with the feeding unit.

Said filtering unit 2 is preferably placed centrally in front of the ostium of the feeder-vessel 11. An improved contact-pressure of the frame 3 against the aortic arch wall, both proximally and distally, is implemented by the division into two sections.

Figure 15:
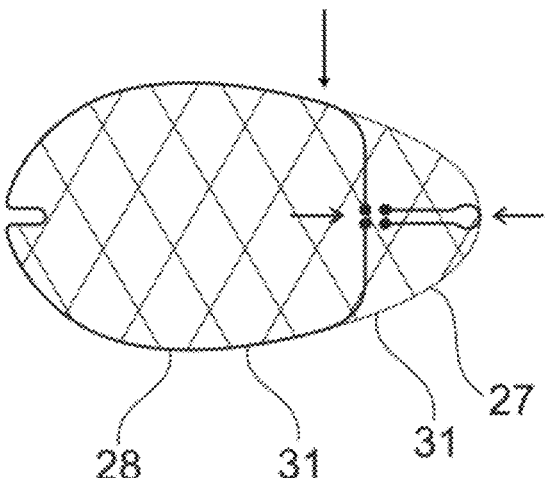

FIG. 15 shows a view from above of the embolic protection device with frame 27, 28 divided into two sections, but a single filter 31. Said filtering unit 2 is likewise preferably placed centrally in front of the ostium of the feeder vessel 11. An improved contact pressure against the aortic arch wall, both proximally and distally, is implemented by the division of the frame 3.

An active device 23 is configured for removing the filtering unit (FIG. 16A), which is routed through the catheter 12 to the user. Upon removal, the proximal area 6 is actively folded in the direction of the feeder vessel 11 by the device 23, and the entire filtering unit 2 can then be removed from the vessel.

Figures 16A, 16B, 16C:
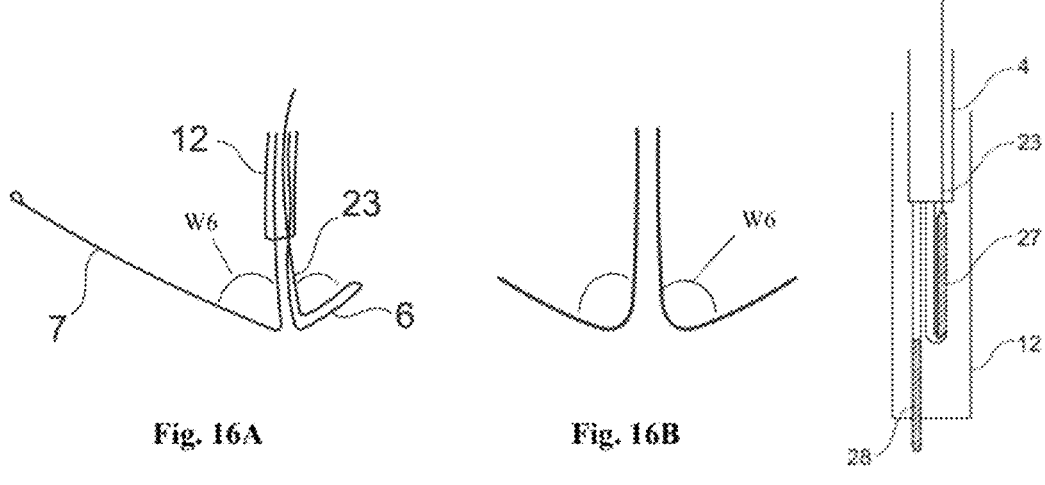

FIG. 16B represents the frontal view of the filtering unit 2 and indicates a potential bending of the filter frames perpendicularly in relation to the direction of flow, which, by drawing towards the aortic roof, causes, inter alia, a widening of the filtering surface and/or an improvement of the abutment against the aortic roof, and thus leads to an increase in the dimensionally stable position and haptic and/or visual feedback.

FIG. 16C shows the embolic protection device in the folded state, upon both insertion and removal, into and front, respectively, the aortic arch 9.

Figures 17A, 17B, 17C:
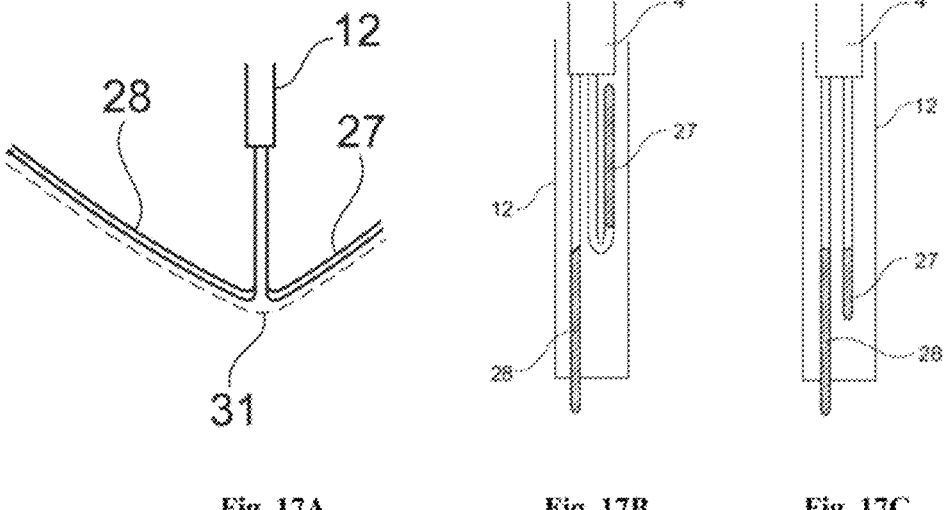

FIG. 17A shows a lateral view of the device upon unfolding, after leaving the catheter 12. The proximal frame 27 and the distal frame 28 are folded out and can be positioned in the aortic arch 9.

FIG. 17B shows the filtering unit 2 in the catheter 12 connected with the feeding unit 4 upon being inserted into the aortic arch 9. In this respect, the proximal frame 27 is folded back, so that the proximal frame 27 and the distal frame 28 are arranged sequentially.

FIG. 17C shows the configuration of the filtering unit 2 in the sluice upon being removed from the aortic arch 9. In this case, the proximal and distal sections are situated parallel to one another.

Figure 18A:
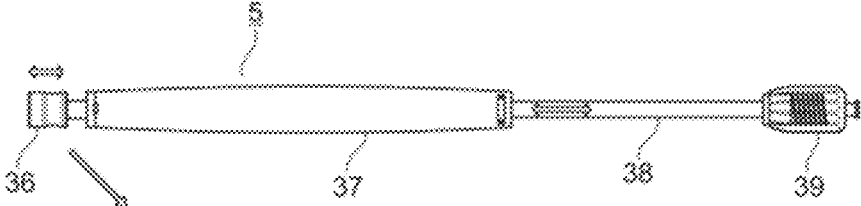

In FIG. 18A, the lateral view of the handle 5 with extended slide between the handle shell 37 and the second connecting piece is shown.

Figure 18B:
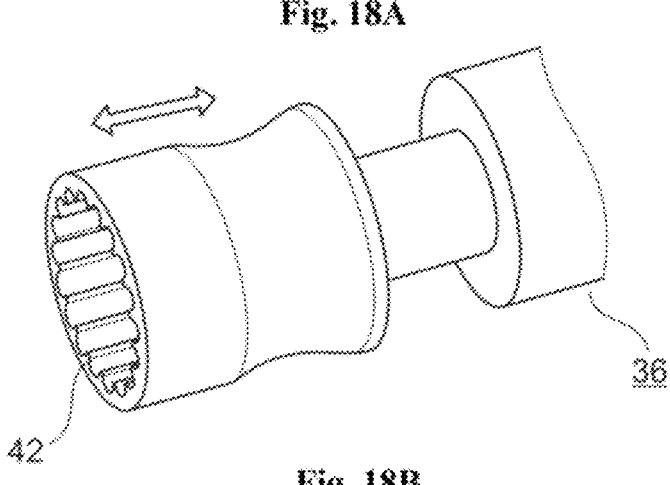

FIG. 18B shows a perspective representation obliquely from the front of the first connecting piece 36 of the handle 5. Notches 42, with which a connection with the blades 40 of the catheter 12 that is to be actively secured can be produced, can be discerned.

In FIG. 19, a cross-section through the lateral view of the second connecting piece 39 of the handle is shown, which includes at least one device for producing reversible connections 43 with the feeding unit 4.

FIG. 20 shows a cross-section through the lateral view of the first connecting piece 36 of the handle 5. The notches 42 on the inside, that interlock with the blades 40 of the catheter 12 are shown, and the catheter 12 is thus fixed in such a way that it cannot rotate.

FIG. 21 shows a cross-section through the frontal view of the first connecting piece 36 of the handle 5 with the catheter 12 inserted, and the blades 40 that interlock with the notches 42.

FIG. 22 shows the lateral view of the handle 5 for a medical device, but in particular for the embolic protection device 1, with a first connecting piece 36, a handle shell 37 and a second connecting piece 39.

The feeding unit, and thus the embolic protection device (1) can be brought into a particular position by means of the slide, so that an advantageous positioning of the filtering unit (2) can be achieved by the feeding unit (4), which runs through the handle (5).

The invention concerns an embolic protection device (1) for inserting into an aortic arch, (9), comprising a filtering unit (2) and a feeding unit (4), wherein the filtering unit (2) comprises a frame (3) and a filter mesh (20) and the filter mesh (20) is arranged on the frame (3), the filtering unit (2) has a proximal area (6) and a distal area (7), wherein the filtering unit (2) is designed in such a way that it can, at least partially, be positioned in the aortic arch (9).

In an enhancement of the embolic protection device (1), the latter is characterised in that, when the filtering unit (2) is appropriately positioned, haptic and/or visual feedback is generated, which signals the final position to the user.

In one enhancement of the embolic protection device (1), the frame (3) comprises two ends (18) and (19) in the proximal area (6), which extend in parallel to one another in the interior of the frame (3) and are connected with the feeding unit (4).

In one enhancement of the embolic protection device (1), the latter is characterised in that the proximal area (6) has an anchorage (16), designed in such a way that the radial rigidity is increased.

In one enhancement of the embolic protection device (1), the distal area (7) is designed to be tapered towards the tip (17), and thus has a streamlined cross-sectional distribution.

In a—likewise independently inventive—enhancement of the embolic protection device (1), a support (21) is configured between the filter mesh (20) and the feeding unit (4), through which the filter mesh (20) is passively drawn to the aortic roof (22) in the expanded state.

In one enhancement of the embolic protection device (1), the support (21) is a spring.

In a—likewise independently inventive—enhancement of the embolic protection device (1), the filter mesh (20) is connected with a device (23), so that the filter mesh (20) can be actively drawn via the device (23) to the aortic roof (22).

In one enhancement of the embolic protection device (1), the device (23) is a wire or a yam.

In one enhancement of the embolic protection device (1), the proximal area (6) can be configured separately from the distal area (7) in the feeder vessel (11), and the distal area (7) separately from the proximal area (6) in the aortic arch (9).

In an enhancement of the embolic protection device (1), the proximal area (6) can be adjusted to the feeder vessel (11) through a change in the direction of curvature in the frame geometry, and can be fixed therein.

In one—likewise independently inventive—enhancement of the embolic protection device (1), the entire filtering unit (2) can be arranged in the aortic arch (9) and, when the filtering unit (2) is appropriately positioned in the aortic arch (9), the proximal area (6) is formed distally of the feeder vessel (11).

In one enhancement of the embolic protection device (1), the ends (18, 19) of the frame (3) in the unfolded state are arranged at an acute angle W1 to the distal filtering level (24), so that, by drawing the frame (3) towards the roof of the aortic arch (22), the latter is moulded in such a way that the width of the end of the proximal area (6) is increased.

In one enhancement of the embolic protection device (1), the ends (18, 19) of the frame (3) are, in the unfolded state, configured at an acute angle W3 to the proximal filtering level (25), so that, by drawing the frame (3) towards the roof of the aortic arch (22), a proximal filtering surface (26) extending in the direction of flow is formed.

In one enhancement of the embolic protection device (1), the filtering unit (2) is divided into two sections, in such a way that the proximal area (6) can be actively and/or passively collapsed, independently of the distal area (7), when the embolic protection device (1) is removed.

In one enhancement of the embolic protection device (1), the filtering unit (2) is divided into two sections in such a way that the proximal area (6) protrudes from the filtering level, so that, by re-shaping the proximal area (6) when positioning the device, a torsion is transmitted to the distal area (7), which increases the contact pressure on the roof of the aortic arch (22).

In one enhancement of the embolic protection device (1), the filtering unit (2) is divided into two sections in such a way that the proximal area (6) protrudes from the filtering level, so that the proximal area (6) is widened when the device is positioned.

In one enhancement of the embolic protection device (1), the filtering unit (2) is divided into two sections in such a way that the ends (18, 19) of the proximal area (6) define an arcuate shape, in such a way that the first part (a) of the arcuate shape is formed in the direction of the distal area (7) and the second part (b) in the direction of the proximal area (6).

In a—likewise independently inventive—enhancement of the embolic protection device (1), the filtering unit (2) is divided into two sections in such a way that the proximal area (6) and the distal area (7) each possess their own frame (27, 28), over which a respective independent filter (29, 30) expands.

In one enhancement of the embolic protection device (1), the second part (b) is connected with the filter mesh (20) and/or with the proximal frame (27) via a device (23), and the proximal area (6) can be actively collapsed in the direction of the feeder vessel (11) via said device (23).

In one—likewise independently inventive—enhancement of the embolic protection device (1), the filtering unit (2) is divided into two sections in such a way that the proximal area (6) and the distal area (7) each possess their own frame (27, 28), and that a single filter (31) expands over both frames.

In one enhancement of the embolic protection device (1), a support (21) is placed between the filter mesh (20) and/or the frame (3) of the proximal area (6), through which the proximal frame (27) can be passively collapsed in the direction of the feeder vessel (11).

In one—likewise independently inventive—enhancement of the embolic protection device (1). the filtering unit (2) is divided into two sections in such a way that a second frame (32) lies in the outer area of the first frame (33) and the second frame (32) is connected with the filter mesh (20) only in the distal area (7) of the first frame (33), and the proximal end (6) of the first frame (33) can be pulled in the direction of the feeder vessel (11), wherein the second frame (32) is drawn to the roof of the aortic arch (22) and a funnel (34) emerges.

In one enhancement of the embolic protection device (1), the frame (3) of the filtering unit (2) is connected with a return device (35), through which the frame can be returned into the catheter (12), and the circumference of the filter mesh (20) exceeds the circumference of the frame (3), wherein the filter mesh (20) is connected with the feeding unit (4), so that, when the filter mesh (20) is pulled in the direction of the feeder vessel (11), a funnel (34) is formed.

A—likewise independently inventive—enhancement concerns a handle (5) for an embolic protection device (1) wherein the handle (5) comprises a first connecting piece (36), a handle shell (37), a slide (38) and/or a second connecting piece (39), wherein the first connecting piece (36) is designed as a connection that is to be actively secured and/or the second connecting piece (39) is designed as a reversible clamping connection.

In one enhancement of the handle (5), the first connecting piece (36) is designed in such a way that a connection that is to be actively secured to a catheter can be produced.

In one enhancement of the handle (5), the connecting piece (36) has notches (42) on the inside, into which the blades (40) of the catheter (12) can be inserted.

In one enhancement of the handle (5), a reversible clamp connection to the feeding unit (4) can be produced by means of the second connecting piece (39).

In one enhancement of the handle (5), the slide (38) is designed in such a way that it can exert a tractive and/or compressive mechanism for loading and positioning devices.

In one enhancement of the handle (5), the slide (38) has a locking device for anchoring, which enables the position of the slide to be adjusted in relation to the handle shell (37).

In one enhancement of the handle (5), the handle (5) includes a haemostatic valve.

In one enhancement of the handle, the handle shell (37) has an interior guide, which can be inserted into the slide (38).

One—likewise independently inventive—enhancement concerns a system consisting of an embolic protection device (1) and a catheter (12).

In one enhancement of the [word missing], the embolic protection device (1) is designed in such a way that it can be passed through the catheter (12).

In one enhancement of the system, the latter contains an embolic protection device (1), a handle (5) and a catheter (12).

In one enhancement of the system, the catheter (12) can be fixed in the handle (5), and the embolic protection device (I) can be passed through the catheter (12) and can be connected with the handle (5) via the feeding unit (4).

A—likewise independently inventive—enhancement concerns a method of using an embolic protection device (1).

A—likewise independently inventive—enhancement concerns a method of using a handle (5).

A—likewise independently inventive—enhancement concerns a method of using a system consisting of an embolic protection device (1) and/or a handle (5) and/or a catheter (12).

LIST OF REFERENCE SIGNS

1 Embolic protection device
2 Filtering unit
3 Frame
4 Feeding unit
5 Handle
6 Proximal area
7 Distal area
8 Aortic section
9 Aortic arch
10 Vascular section
11 Feeder vessel
12 Catheter
13 Arrows to designate the streamlined cross-sectional distribution
14 Position of the reduced interaction with devices in the aortic arch
15 Position for changing the direction of curvature
16 Anchorage
17 Distal tip
18 End of the frame
19 End of the frame
20 Filter mesh
21 Support
22 Roof of the aortic arch
23 Device
24 Distal filtering level
25 Proximal filtering level
26 Proximal filtering surface
27 Proximal frame
28 Distal frame
29 Proximal filter
30 Distal filter
31 Individual filter
32 Second frame
33 First frame
34 Funnel
35 Return vice
36 First connecting piece
37 Handle shell
38 Slide
39 Second connecting piece
40 Blades
41 Area of radial stability
42 Notches
43 Device for producing reversible connections
First part, arcuate shape a)
Second part, arcuate shape b)
W1 Angle
W2 Angle
W3 Angle
W4 Angle W5 Angle
W6 Angle
T Torsion
E Increase in the width

The invention claimed is:

1. A method of positioning an embolic protection device in an aortic arch, the method comprising:
providing a filtering unit;
providing a feeding unit coupled to the filtering unit;
wherein the filtering unit comprises a frame forming a loop and a filter mesh arranged along the loop of the frame,
wherein the loop of the frame comprises a proximal area and a distal area, and
introducing the filtering unit at least partially into the aortic arch, wherein the filtering unit is introduced into the aortic arch from a feeder vessel; and
expanding the filtering unit into an expanded state using the feeding unit;
wherein, after the filtering unit is expanded, the proximal area of the loop and at least a portion of the filter mesh is positioned in the feeder vessel separately from the distal area positioned in the aortic arch.

2. The method of claim 1, further comprising generating haptic or visual feedback when the filtering unit is appropriately positioned to signal a final position to a user.

3. The method of claim 1, wherein the frame comprises two proximal ends extending in parallel to one another and connected to the feeding unit via an area.

4. The method of claim 1, wherein the proximal area comprises an anchorage, such that a radial rigidity of the frame is increased.

5. The method of claim 1, further comprising passively drawing the filter mesh to an aortic roof, using a support placed between the filter mesh and the feeding unit, when the filter mesh is in an expanded state.

6. The method of claim 5, wherein the support is a spring, a rubber component, nitinol or an elastic material.

7. The method of claim 1, further comprising actively drawing the filter mesh to an aortic roof using a device coupled to the filter mesh.

8. The method of claim 7, wherein the device is a wire, a yarn or a chain.

9. The method of claim 1, further comprising fixing the proximal area in the feeder vessel, the proximal area configured to adjust to the feeder vessel through a change in a direction of curvature in the frame.

10. The method of claim 1, further comprising returning the frame of the filtering unit to a catheter using a return device coupled to the frame.

11. The method of claim 1, wherein the filtering unit comprises a first frame and a second frame, such that the second frame lies in an outer area of the first frame.

12. The method of claim 1, wherein a circumference of the filter mesh exceeds a circumference of the frame, wherein the filter mesh is connected to the feeding unit such that a wedge is formed when the filter mesh is pulled toward the feeder vessel.

13. The method of claim 1, further comprising providing a handle coupled to the feeding unit, the handle comprising a first connecting piece, a handle shell, a slide, and a second connecting piece.

14. The method of claim 13, wherein the handle is coupled to a catheter through which the filtering unit is introduced into the aortic arch.

15. The method of claim 14, wherein the first connecting piece of the handle comprises notches on an inside surface of the first connecting piece that receive blades of the catheter.

16. The method of claim 13, wherein the second connecting piece reversibly clamps to the feeding unit.

17. The method of claim 13, wherein positioning the filtering unit comprises operating the slide to exert a pull and/or push force on the feeding unit.

18. The method of claim 13, further comprising anchoring the slide with a locking device such that a position of the slide is adjustable in relation to the handle shell.

19. The method of claim 13, wherein the handle further comprises a haemostatic valve.

20. The method of claim 13, wherein the handle shell comprises an interior guide tube insertable into the slide.

21. The method of claim 1, wherein the filtering unit is introduced into the aortic arch through a catheter.

22. The method of claim 14, further comprising actively securing the first connecting piece of the handle to the catheter.

* * * * *